US00PP30241P3

(12) United States Plant Patent
Biancheri

(10) Patent No.: US PP30,241 P3
(45) Date of Patent: Feb. 26, 2019

(54) ***RANUNCULUS* PLANT NAMED 'ABAIRESEKUI'**

(50) Latin Name: *Ranunculus asiaticus*
Varietal Denomination: ABAIRESEKUI

(71) Applicant: Alberto Biancheri, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 15/731,512

(22) Filed: Jun. 20, 2017

(65) Prior Publication Data

US 2018/0042159 P1 Feb. 8, 2018

(30) Foreign Application Priority Data

Aug. 5, 2016 (QZ) ..... PBR 2016/1917

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/02; A01H 5/00; A01H 6/72
See application file for complete search history.

(56) References Cited

PUBLICATIONS

Missouri Botanica Garden *Ranunculus asiaticus,* retrieved on May 15, 2018, retrieved from the Internet at http://www.missouribotanicalgarden.org/PlantFinder/PlantFinderDetails.aspx?kempercode=a471, 2 pp. (Year: 2018).*

* cited by examiner

*Primary Examiner* — June Hwu
(74) *Attorney, Agent, or Firm* — Cassandra Bright

(57) ABSTRACT

A new and distinct *Ranunculus* cultivar named 'ABAIRESEKUI' is disclosed, characterized by the production of large flowers that are uniquely streaked purple and white. Petals have a distinctive dentation. The new variety is a *Ranunculus*, normally produced as a cut flower and also potentially useful as an ornamental plant.

2 Drawing Sheets

Latin name of the genus and species: *Ranunculus asiaticus*.

Variety denomination: 'ABAIRESEKUI'.

BACKGROUND OF THE INVENTION

The new *Ranunculus* cultivar is a product of a planned breeding program conducted by the inventor, Alberto Biancheri in Camporosso Mare, Italy. The cross resulting in this new variety was made during 2008.

The seed parent is the, unpatented, proprietary variety referred to as *Ranunculus* 'B.str.07A'. The pollen parent is the unpatented, proprietary variety referred to as *Ranunculus* 'RsStr05D'. The new variety was discovered in 2013 by the inventor in a group of seedlings resulting from the 2008 crossing, in a research greenhouse in Camporosso Mare, Italy.

Asexual reproduction of the new cultivar was first performed by vegetative division of buds sprouting from the tuberous root of the selected plant. Subsequent propagation has been performed by tissue culture. First propagation took place at a research greenhouse in Camporosso Mare, Italy in 2013 and has shown that the unique features of this cultivar are stable and reproduced true to type in multiple successive generations.

SUMMARY OF THE INVENTION

The cultivar 'ABAIRESEKUI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABAIRESEKUI' These characteristics in combination distinguish 'ABAIRESEKUI' as a new and distinct *Ranunculus* cultivar:

1. Unique flower color, streaked white and purple.
2. Petal margins uniquely serrate.
3. Extra-large flower size.

PARENT COMPARISON

Plants of the new cultivar 'ABAIRESEKUI' are similar to plants of the seed parent, in most horticultural characteristics, however, plants of the new cultivar 'ABAIRESEKUI' differ in the following;

1. The new variety produces a large flower.
2. The new variety produces flowers of a different color.

Plants of the new cultivar 'ABAIRESEKUI' are similar to plants of the pollen parent, in most horticultural characteristics, however, plants of the new cultivar 'ABAIRESEKUI' differ in the following;

1. The new variety produces flowers of a different color.

COMMERCIAL COMPARISON

Plants of the new cultivar 'ABAIRESEKUI' are comparable to the unpatented commercial variety *Ranunculus*

'Aazur White Striped'. The two *Ranunculus* varieties are similar in most horticultural characteristics; however, the new variety 'ABAIRESEKUI' differs in the following:

1. The new variety has significantly more streaking of color on the petals.
2. The new variety has a larger flower size.

BRIEF DESCRIPTION OF THE PHOTOGRAPHS

Figure 1:
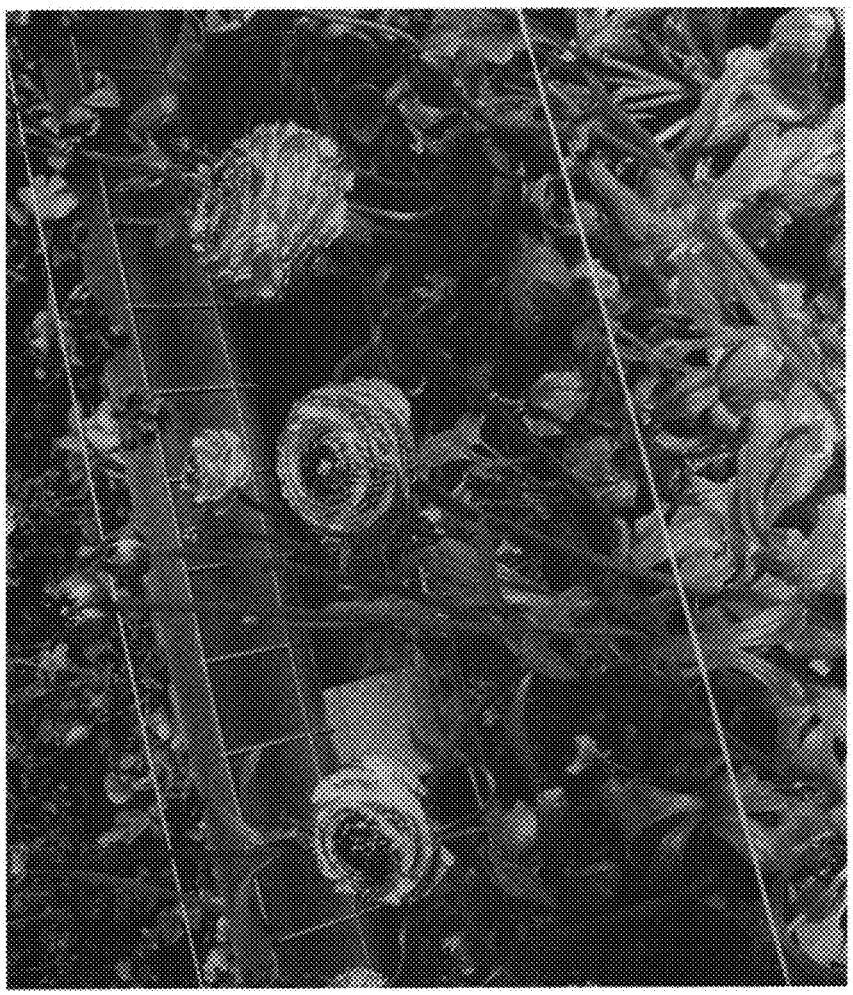

The accompanying photograph in FIG. 1 illustrates in full color flowering plants of the new variety at approximately five months old, grown in a greenhouse.

Figure 2:
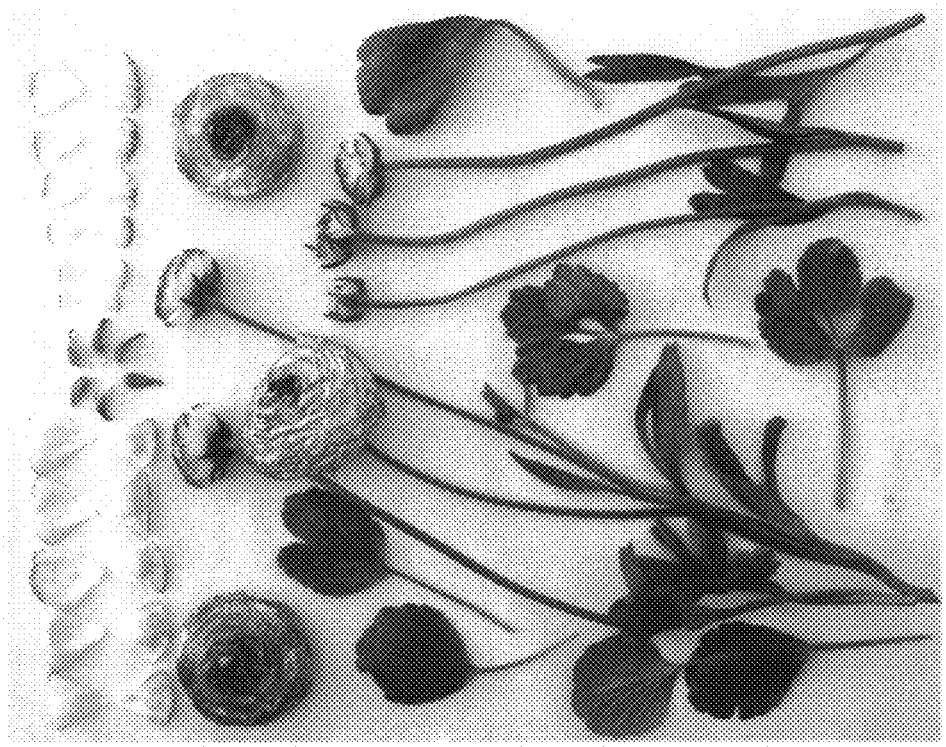

FIG. 2 illustrates a close up of plant parts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 'ABAIRESEKUI' plants grown in a greenhouse Camporosso Mare, Italy. The plant described has been cultivated under glass, planted in the months of September and described in the month of February. One must always refer to these conditions of season and culture, when considering the present description. By reason of different climate or culture conditions, differences may arise between certain characteristics of the plant and the corresponding characteristics of the description. It should be considered as normal and do not modify the essence of the present invention because it will possible to identify the plant by means of the totality of the characteristics given in the description. The rhizome has been planted on raised benches in a peat and pomice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* 'ABAIRESEKUI'.

PROPAGATION

Time to rooting: 15 days at approximately 10-12° C.

Time to produce a rooted plantlet: 20 days.

Root description: Tuberous roots. Quantity of tubers varies significantly with environmental conditions and age. Roots are white and tan, not accurately measured with the R.H.S. chart.

PLANT

Age of plant described: Plant 150 days old from the planting of the pre-sprouted tuberous root.

Growth habit: Herbaceous perennial, robust plant, semi-erect vegetation.

Height to top flower: 50 to 60 cm.

Plant spread: 40 to 50 cm.

Growth rate: Medium.

Branching characteristics: Main floral stems grow from a basal rosette, with 1 or 2 lateral branches, each one of which has a flower.

Length of lateral branches: Average range 40 to 50 cm.

Diameter of lateral branches: Average range 0.8 to 1.0 cm.

Texture of lateral branches: Slightly tomentose.

Internode length: Internodes are extremely close together forming a basal rosette.

Strength of lateral branches: Medium.

Color of lateral branches: Near RHS Yellow Green 146B.

Aspect/angle of branches: 25° to 30° from center of plant.

Number of leaves per lateral branch: Usually 2 or 4.

FOLIAGE

Leaf: The leaves, usually numerous, have a marked heterophyllia (Significant variation in leaf shape, size and arrangement on a same plant), Simple, biternate and ternate leaves appear on the same plant, in relation to the degree of development (young leaf and mature leaf) and their position on the plant (basal leaf — leaf at the base of the plant — and cauline leaf — leaf inserted at the nodes of the floral stems).

Leaf at the base of the plant:

*Arrangement.*—Simple (young leaf, YL); Biternate (mature leaf, ML).

*Average length.*—20 to 24 cm.

*Average width.*—10 to 15 cm.

*Overall shape of blade.*—Obovate (young leaf); Palmatipartite (mature leaf). Young leaves are generally not lobed; mature leaves are generally divided in 3 parts, each one of which is further divided in 3 or more lobes.

*Apex.*—Rounded.

*Base.*—Rounded.

*Margin.*—Crenate (young leaf); Dentate (mature leaf).

*Texture of top surface.*—Slightly tomentose, Rugose.

*Texture of bottom surface.*—Glabrous to slightly tomentose. Rugose.

*Appearance of top surface.*—Glossy.

*Appearance bottom surface.*—Glossy.

*Leaf internode length.*—The internodes are extremely close together forming a basal rosette.

*Color.*—Young foliage upper side: RHS Green 137C. Young foliage under side: RHS Yellow Green 147B. Mature foliage upper side: RHS Green 137C. Mature foliage under side: RHS Yellow Green 147B.

*Venation.*—Type: Dichotomous; plunging in to the blade at the upper surface; raised on the lower surface. Venation color upper side: RHS Yellow Green 146B. Venation color under side: RHS Yellow Green 146B.

*Petiole.*—Petiole: Long, tubular, rigid. Length: Average range 12 to 15 cm. Diameter: 0.4 to 0.6 cm. Pubescence: Slightly tomentose. Color: RHS Yellow Green 146B.

Leaf inserted at the nodes of the floral stems (sl):

*Arrangement.*—Simple.

*Average length.*—15 to 20 cm.

*Average width.*—3 to 13 cm.

*Overall shape of blade.*—Lanceolate.

*Dissected leaves, describe lobes, quantity of dissection.*—Generally simple or divided in 2 or 3 lobes.

*Apex.*—Acute.

*Base.*—Acute.

*Attachment.*—Petiolate

*Margin.*—Dentate.

*Texture of top surface.*—Slightly tomentose, rugose.

*Texture of bottom surface.*—Slightly tomentose, rugose.

*Appearance of top surface.*—Matte.

*Appearance bottom surface.*—Glossy.

*Leaf internode length.*—9 to 15 cm.

*Color.*—Foliage upper side: RHS Green 137B. Foliage under side: Yellow Green (RHS 146B).

*Venation.*—Type: Longitudinal, deeply plunging in to the limb at the upper surface and very raised on the limb at the lower surface. Venation color upper side: Yellow Green (RHS 146B). Venation color under side: Yellow Green (RHS 146B).

*Petiole.*—Petiole: Long, slightly flat, rigid. Length: 3 to 9 cm. Diameter: 0.6-0.8 cm. Pubescence: A little tomentose.

*Color.*—Yellow Green (RHS 146B).

FLOWER

Bloom period: Winter and Spring time.

Vase life (cut flower): 10 to 15 days.

Average number of flowers per plant: 5-7.

Bud:

*Closed bud (cb).*—Shape: Flattened globular with sharp point. Length: 1.4 to 2.3 cm. Diameter: 1.0 to 1.6 cm. Color: Green (RHS 137A); Purple (RHS N79A) along the venations.

*Slightly open bud (ob).*—Shape: Flattened globular. Length: 2.3 to 2.5 cm. Diameter: 2.3 to 2.7 cm. Color: Yellow Green (RHS 144D); Dark Purplish Red (RHS N79A) at the margins.

Flower size ($of_{1,2}$):

*Diameter.*—8 to 12 cm.

*Height.*—2.8 to 3.6 cm.

Corolla ($of_{1,2}$): Round, regular, in the form of a flat section with slightly festooned edges.

Petals:

*Arrangement.*—Imbricated, arranged on the receptacle in very tight verticils. The size of the petals is quite variable, according to the position in the corolla, decreasing from the exterior toward the center. The average size of a fully developed petal is as follows.

*Length.*—3.5 to 4.5 cm.

*Width.*—4.0 to 5.0 cm.

*Quantity.*—Double flower, petals are very numerous and variable. From 120 to 200, per flower.

*Texture all surfaces.*—Silky, thin, resistant to tearing.

*Apex.*—Dentate.

*Shape.*—Obdeltoid.

*Margin.*—Entire along sides, dentate at apex.

*Aspect.*—Triangular concave with a little reflexed apex when flower is fully opened.

Color when opening (cf):

*Upper surface.*—Dark Purplish Red (RHS N79A) at the margin; Greenish Yellow (RHS1D) fading to Yellow-White 158D from the base towards the center.

*Lower surface.*—Dark Purplish Red (RHS N79A) at the margin; Light Reddish Purple (RHS NN74C) near the margin; Greenish Yellow (RHS1D) fading to White N155D from the base towards the center.

Color fully opened ($of_1$):

*Upper surface ($pu_1$).*—Purple (RHS N79B) at the margin; fading to a thin flush of Red-Purple 64B, majority of surface White N155B.

*Lower surface ($pl_1$).*—Purple (RHS N79B) at the margin; fading to Red-Purple (RHS NN74C) from the margin to the center; Base White N155B.

Other cultural improvements or features: In this variety, the colors of the corolla could present a lack of Purple tones and an increase of Green tones. This is already noticeable in the flowers that are opening and is present in those that are wide open ($OF_2$; $PU_2$, $PL_2$). This variation of color, partially typical of this variety, is accentuated in particular growing conditions, in relation to light exposure, to the temperature and to the different composition of fertilizers used by the various farms.

Calyx/sepals (s):

*Quantity per flower.*—6.

*Shape.*—Concave, moderately incurved.

*Length.*—2.4 to 3.0 cm.

*Width.*—0.8 to 1.2 cm.

*Apex.*—Acute.

*Base.*—Flat to slightly rounded.

*Margin.*—Entire; dentate at the apex.

*Texture.*—Lower surface is tomentose; Upper surface is glabrous.

*Color upper surface.*—Green (RHS 138B).

*Color lower surface.*—Green (RHS 137B); Red Purple (RHS 71A) along venation.

Peduncle: None.

Pedicel:

*Length.*—53 to 57 cm.

*Diameter.*—1.0 to 1.2 cm.

*Color.*—Yellow Green (RHS 146B).

*Orientation.*—Upright, straight, rigid.

*Pubescence.*—Slightly tomentose.

Fragrance: None.

REPRODUCTIVE ORGANS

Androecium:

*Stamens.*—Irregular, reduced and malformed. Almost completely transformed to petals.

Gynoecium: Apocarpous gynoecium in the center the corolla, composed of numerous short, (approximately less than 1 cm), fused pistils. Colored Yellow Green (RHS N144D) and Purple (RHS N79B). Fusion of pistils prevents accurate measurement of quantity.

Nectar gland: Absent.

OTHER CHARACTERISTICS

Seeds and fruits: Seeds and fruit production not observed.

Disease/pest resistance: Neither resistance nor susceptibility to normal diseases and pests of *Ranunculus* has been observed.

Temperature tolerance: Upper and lower temperature tolerance not observed, plants have been grown in a climate controlled greenhouse. *Ranunculus asiaticus* typically tolerates temperatures within USDA Zones 7 to 11.

What is claimed is:

1. A new and distinct cultivar of *Ranunculus* plant named 'ABAIRESEKUI' as herein illustrated and described.

* * * * *